United States Patent [19]
Siebers et al.

[11] Patent Number: 5,984,911
[45] Date of Patent: Nov. 16, 1999

[54] ABSORBENT ARTICLE HAVING AN IMPROVED FASTENING SYSTEM

[75] Inventors: Bruce Michael Siebers, Appleton; Gary Lee Travis, Oshkosh; Thomas Walter Odorzynski, Green Bay, all of Wis.

[73] Assignee: Kimberly-Clark Worldwide, Inc., Neenah, Wis.

[21] Appl. No.: 08/233,843

[22] Filed: Apr. 26, 1994

Related U.S. Application Data

[60] Division of application No. 07/906,016, Jun. 26, 1992, Pat. No. 5,318,555, which is a continuation-in-part of application No. 07/954,094, Sep. 30, 1992, Pat. No. 5,403,302, which is a division of application No. 07/627,874, Dec. 13, 1990, Pat. No. 5,176,671, which is a continuation of application No. 07/287,746, Dec. 20, 1988, abandoned, said application No. 07/906,016, is a continuation-in-part of application No. 07/628,251, Dec. 17, 1990, abandoned.

[51] Int. Cl.$^6$ .................................................. A61F 13/15
[52] U.S. Cl. ......................... 604/391; 604/358; 604/386
[58] Field of Search ........................ 604/358, 385.1, 604/385.2, 386, 389–391; 27/442, 447, 448, 452

[56] References Cited

U.S. PATENT DOCUMENTS

| B1 636,207 | 11/1989 | Buell ........................................ 604/370 |
| 2,511,406 | 6/1950 | Israel ........................................ 128/284 |

(List continued on next page.)

FOREIGN PATENT DOCUMENTS

| 74/74625 | 10/1974 | Australia . |
| 0 013 463 A1 | 7/1980 | European Pat. Off. . |
| 0 080 647 A1 | 6/1983 | European Pat. Off. . |
| 0 131 490 A1 | 1/1985 | European Pat. Off. . |
| 0 155 155 A2 | 9/1985 | European Pat. Off. . |

(List continued on next page.)

OTHER PUBLICATIONS

Update 84 "Absorbent Products Markets Part 1, (Tampons, Diapers, Feminine Pads)," vol. 1, Diapers; published by Marketing/Technology Service, Dec. 1984.

"And Velcro Fitted Nappies," *Medical Textiles,* vol. 1, No. 1, May 1984, pp. 11–12.

"Easy–To–Fit Reusable Diaper," *Medical Textiles,* vol. 3, No. 1, May 1986, pp. 9–10.

"A Gripping Success," *Dupont Magazine,* May/Jun. 1985, pp. 26–27.

"Hook & Loop Fasteners," written by Brian Lambert, *Industrial Fabric Products Review,* Sep. 1985, pp. 45–47.

"Closures Become Fashion," written by Timothy Wilson, *Bobbin Magazine,* Dec. 1986, pp. 94–98.

"Closing In On New Markets," written by Dr. Annette J. Fraser, *Bobbin Magazine,* Dec. 1987, pp. 104–109.

"AMF Hook & Loop Tape Attacher Programmed For Industrial Uses," *Bobbin Magazine,* Apr. 1987, p. 130.

"Your Baby's First Year" (Time–Life Book Inc. 1986), pp. 38–41.

"Consumer Guide® Baby Equipment Buying Guide" Signet (Copyright Publications International, Ltd. 1985), pp. 106–109.

(List continued on next page.)

*Primary Examiner*—John G. Weiss
*Assistant Examiner*—Dennis Ruhl

[57] ABSTRACT

An absorbent or other article including a tensioning system for joining portions of the article together. The system includes a plurality of hook members attached on one portion of the article, and a plurality of loop members attached to a loop panel wherein the loop panel may be intermittently attached to the article.

19 Claims, 7 Drawing Sheets

U.S. PATENT DOCUMENTS

| | | | |
|---|---|---|---|
| 2,524,842 | 10/1950 | Slamon et al. | 154/41 |
| 2,649,858 | 8/1953 | Le Bolt | 128/284 |
| 2,936,758 | 5/1960 | Csulits | 128/284 |
| 3,081,772 | 3/1963 | Brooks et al. | 128/287 |
| 3,110,312 | 11/1963 | Wirth | 128/287 |
| 3,138,841 | 6/1964 | Naimer | 24/204 |
| 3,141,461 | 7/1964 | Farris | 128/284 |
| 3,146,778 | 9/1964 | Krawiec | 128/349 |
| 3,147,528 | 9/1964 | Erb | 24/204 |
| 3,150,664 | 9/1964 | Noel | 128/287 |
| 3,180,335 | 4/1965 | Duncan et al. | 128/287 |
| 3,196,511 | 7/1965 | Kintner | 24/204 |
| 3,315,676 | 4/1967 | Cooper | 128/287 |
| 3,318,632 | 5/1967 | Struble et al. | 297/220 |
| 3,359,980 | 12/1967 | Rosenblatt | 128/284 |
| 3,559,648 | 2/1971 | Mason, Jr. | 128/287 |
| 3,572,342 | 3/1971 | Lindquist et al. | 128/287 |
| 3,599,640 | 8/1971 | Larson | 128/286 |
| 3,618,608 | 11/1971 | Brink | 128/287 |
| 3,620,217 | 11/1971 | Gellert | 128/284 |
| 3,630,201 | 12/1971 | Endres | 128/287 |
| 3,653,381 | 4/1972 | Warnken | 128/284 |
| 3,694,867 | 10/1972 | Stumpf | 24/204 |
| 3,710,425 | 1/1973 | Brumlik | 24/204 |
| 3,779,246 | 12/1973 | Mesek et al. | 128/287 |
| 3,800,796 | 4/1974 | Jacob | 604/386 |
| 3,825,006 | 7/1974 | Ralph | 128/287 |
| 3,840,945 | 10/1974 | Brumlik | 24/204 |
| 3,848,594 | 11/1974 | Buell | 128/284 |
| 3,863,304 | 2/1975 | Brumlik | 24/204 |
| 3,869,761 | 3/1975 | Schaar | 24/73 VA |
| 3,879,835 | 4/1975 | Brumlik | 29/412 |
| 3,882,871 | 5/1975 | Taniguchi | 128/287 |
| 3,889,322 | 6/1975 | Brumlik | 24/204 |
| 3,899,803 | 8/1975 | Brumlik | 24/204 |
| 3,900,652 | 8/1975 | Uraya et al. | 428/92 |
| 3,913,183 | 10/1975 | Brumlik | 24/204 |
| 3,920,018 | 11/1975 | Schaar | 128/287 |
| 3,922,455 | 11/1975 | Brumlik | 428/85 |
| 3,927,674 | 12/1975 | Schaar | 128/287 |
| 3,931,666 | 1/1976 | Karami | 24/73 VA |
| 3,950,824 | 4/1976 | Karami | 24/67 AR |
| 3,955,575 | 5/1976 | Okuda | 128/284 |
| 3,963,029 | 6/1976 | Brooks | 128/287 |
| 3,989,048 | 11/1976 | Cepuritis et al. | 128/287 |
| 4,005,712 | 2/1977 | Karami | 128/284 |
| 4,014,340 | 3/1977 | Cheslow | 128/287 |
| 4,022,210 | 5/1977 | Glassman | 128/284 |
| 4,036,233 | 7/1977 | Kozak | 128/287 |
| 4,047,530 | 9/1977 | Karami | 128/287 |
| 4,049,001 | 9/1977 | Tritsch | 128/287 |
| 4,050,463 | 9/1977 | Schaar | 128/287 |
| 4,051,854 | 10/1977 | Aaron | 128/284 |
| 4,056,281 | 11/1977 | Byrnes | 297/220 |
| 4,074,397 | 2/1978 | Rosin | 24/73 AS |
| 4,081,301 | 3/1978 | Buell | 156/164 |
| 4,114,621 | 9/1978 | Mims, Jr. | 128/288 |
| 4,127,132 | 11/1978 | Karami | 128/287 |
| 4,158,906 | 6/1979 | Watson | 24/83 |
| 4,166,464 | 9/1979 | Korpman | 128/287 |
| 4,169,303 | 10/1979 | Lemelson | 24/204 |
| 4,180,890 | 1/1980 | Brumlik | 24/204 |
| 4,205,679 | 6/1980 | Repke et al. | 128/287 |
| 4,229,835 | 10/1980 | Shaw | 2/406 |
| 4,230,113 | 10/1980 | Mehta | 128/287 |
| 4,241,462 | 12/1980 | Tagawa et al. | 2/406 |
| 4,259,957 | 4/1981 | Sonenstein et al. | 128/287 |
| 4,290,174 | 9/1981 | Kalleberg | 24/204 |
| 4,299,223 | 11/1981 | Cronkrite | 128/287 |
| 4,322,875 | 4/1982 | Brown et al. | 24/204 |
| 4,338,939 | 7/1982 | Daville | 128/286 |
| 4,352,355 | 10/1982 | Mesek et al. | 128/287 |
| 4,380,450 | 4/1983 | Reich | 604/386 |
| 4,381,781 | 5/1983 | Sciaraffa et al. | 604/372 |
| 4,388,075 | 6/1983 | Mesek et al. | 604/385 |
| 4,397,645 | 8/1983 | Buell | 604/380 |
| 4,402,690 | 9/1983 | Redfern | 604/391 |
| 4,410,327 | 10/1983 | Baggaley | 604/391 |
| 4,425,128 | 1/1984 | Motomura | 604/381 |
| 4,430,086 | 2/1984 | Repke | 604/385 |
| 4,475,912 | 10/1984 | Coates | 604/385 |
| 4,509,512 | 4/1985 | LeClercq | 128/160 |
| 4,522,874 | 6/1985 | Pommez | 428/284 |
| 4,537,591 | 8/1985 | Coates | 604/391 |
| 4,541,154 | 9/1985 | Ito et al. | 24/442 |
| 4,560,381 | 12/1985 | Southwell | 604/396 |
| 4,568,342 | 2/1986 | Davis | 604/391 |
| 4,568,344 | 2/1986 | Suzuki et al. | 604/389 |
| 4,573,986 | 3/1986 | Minetola et al. | 604/366 |
| 4,576,599 | 3/1986 | Lipner | 604/390 |
| 4,576,601 | 3/1986 | Brain | 604/398 |
| 4,577,591 | 3/1986 | Wesseldine | 119/143 |
| 4,578,066 | 3/1986 | O'Connor | 604/366 |
| 4,581,772 | 4/1986 | Smith | 2/111 |
| 4,585,450 | 4/1986 | Rosch et al. | 604/390 |
| 4,596,568 | 6/1986 | Flug | 604/369 |
| 4,604,096 | 8/1986 | Dean et al. | 604/385 A |
| 4,609,581 | 9/1986 | Ott | 428/100 |
| 4,610,678 | 9/1986 | Weisman et al. | 604/368 |
| 4,610,680 | 9/1986 | LaFleur | 604/385 A |
| 4,610,682 | 9/1986 | Kopp | 604/385 R |
| 4,615,695 | 10/1986 | Cooper | 604/385 A |
| 4,617,022 | 10/1986 | Pigneul et al. | 604/391 |
| 4,623,339 | 11/1986 | Ciraldo et al. | 604/359 |
| 4,626,305 | 12/1986 | Suzuki et al. | 156/164 |
| 4,639,949 | 2/1987 | Ales et al. | 2/400 |
| 4,642,110 | 2/1987 | Dudek | 604/385.1 |
| 4,642,819 | 2/1987 | Ales et al. | 2/400 |
| 4,646,362 | 3/1987 | Heran et al. | 2/400 |
| 4,650,481 | 3/1987 | O'Connor et al. | 604/380 |
| 4,657,539 | 4/1987 | Hasse | 604/385 A |
| 4,661,102 | 4/1987 | Shikata et al. | 604/385 A |
| 4,662,877 | 5/1987 | Williams | 604/385 A |
| 4,671,793 | 6/1987 | Hults et al. | 604/385 R |
| 4,673,402 | 6/1987 | Weisman et al. | 604/368 |
| 4,675,015 | 6/1987 | Brown | 604/385 R |
| 4,680,030 | 7/1987 | Coates et al. | 604/391 |
| 4,681,581 | 7/1987 | Coates | 604/391 |
| 4,687,477 | 8/1987 | Suzuki et al. | 604/385 A |
| 4,695,278 | 9/1987 | Lawson | 604/385 A |
| 4,699,622 | 10/1987 | Toussant et al. | 604/389 |
| 4,701,172 | 10/1987 | Stevens | 604/385 A |
| 4,701,179 | 10/1987 | Kellenberger et al. | 604/394 |
| 4,704,116 | 11/1987 | Enloe | 604/385 A |
| 4,704,117 | 11/1987 | Mitchell | 604/391 |
| 4,705,710 | 11/1987 | Matsuda | 428/92 |
| 4,710,414 | 12/1987 | Northrup et al. | 428/43 |
| 4,725,473 | 2/1988 | Van Gompel et al. | 428/156 |
| 4,728,326 | 3/1988 | Gilles | 604/391 |
| 4,738,677 | 4/1988 | Foreman | 604/385 R |
| 4,743,246 | 5/1988 | Lawson | 604/385 A |
| 4,753,649 | 6/1988 | Pazdernik | 604/389 |
| 4,753,650 | 6/1988 | Williams | 604/389 |
| 4,753,840 | 6/1988 | Van Gompel | 428/171 |
| 4,761,318 | 8/1988 | Ott et al. | 428/85 |
| 4,770,656 | 9/1988 | Proxmire et al. | 604/393 |
| 4,770,917 | 9/1988 | Tochacek et al. | 428/95 |
| 4,772,282 | 9/1988 | Oakley | 604/385.1 |
| 4,773,906 | 9/1988 | Krushel | 604/391 |
| 4,776,068 | 10/1988 | Smirlock et al. | 24/442 |
| 4,778,701 | 10/1988 | Pape et al. | 428/40 |
| 4,795,452 | 1/1989 | Blaney et al. | 604/385.1 |
| 4,795,454 | 1/1989 | Dragoo | 604/385.2 |
| 4,808,176 | 2/1989 | Kielpikowski | 604/385.2 |
| 4,822,435 | 4/1989 | Igaue et al. | 156/164 |
| 4,834,738 | 5/1989 | Kielpikowski et al. | 604/385.2 |
| 4,834,740 | 5/1989 | Suzuki et al. | 604/385.2 |
| 4,834,742 | 5/1989 | Wilson et al. | 604/389 |
| 4,835,795 | 6/1989 | Lonon | 2/408 |
| 4,846,815 | 7/1989 | Scripps | 604/391 |

| | | | | | | |
|---|---|---|---|---|---|---|
| 4,846,823 | 7/1989 | Enloe .................................. 604/385.2 | | 2 606 257 | 5/1988 | France . |
| 4,847,134 | 7/1989 | Fahrenkrug et al. ................... 428/138 | | 88591 | 12/1921 | Germany . |
| 4,850,988 | 7/1989 | Aledo et al. ......................... 604/385.1 | | 906 365 | 3/1954 | Germany . |
| 4,854,136 | 8/1989 | Coslovi et al. ........................... 66/191 | | 1 070 779 | 12/1959 | Germany . |
| 4,857,067 | 8/1989 | Wood et al. .............................. 604/389 | | 2 322 492 | 11/1974 | Germany . |
| 4,861,399 | 8/1989 | Rajala et al. .............................. 156/66 | | 2 504 210 | 8/1975 | Germany . |
| 4,861,652 | 8/1989 | Lippert et al. ........................... 428/284 | | 33 17 117 | 6/1984 | Germany . |
| 4,869,724 | 9/1989 | Scripps ................................... 604/389 | | 3419623A1 | 11/1985 | Germany ........................... 604/385.1 |
| 4,870,725 | 10/1989 | Dubowik ................................. 24/442 | | 35 33 881 | 4/1986 | Germany . |
| 4,880,420 | 11/1989 | Pomparelli .......................... 604/385.1 | | 63-2708 | 1/1968 | Japan . |
| 4,883,480 | 11/1989 | Huffman et al. ..................... 604/385.1 | | 49-115139 | 10/1974 | Japan . |
| 4,884,713 | 12/1989 | Handler ................................ 220/23.4 | | 49-120438 | 10/1974 | Japan . |
| 4,887,338 | 12/1989 | Handler .................................. 24/306 | | 49-144438 | 12/1974 | Japan . |
| 4,887,339 | 12/1989 | Bellanger ................................ 24/575 | | 53-158440 | 12/1978 | Japan . |
| 4,891,868 | 1/1990 | Watanabe ................................ 24/691 | | 54-105738 | 7/1979 | Japan . |
| 4,892,528 | 1/1990 | Suzuki et al. ........................ 604/385.2 | | 56-11243 | 2/1981 | Japan .............................. B32B 5/18 |
| 4,894,060 | 1/1990 | Nestegard ............................... 604/391 | | 57-138908 | 8/1982 | Japan . |
| 4,895,568 | 1/1990 | Enloe .................................. 604/385.2 | | 57-161101 | 10/1982 | Japan . |
| 4,904,251 | 2/1990 | Igaue et al. .......................... 604/385.2 | | 57-191303 | 11/1982 | Japan . |
| 4,909,803 | 3/1990 | Aziz et al. ........................... 604/385.2 | | 57-191304 | 11/1982 | Japan ............................. A41B 13/02 |
| 4,916,005 | 4/1990 | Lippert et al. ........................... 428/192 | | 58-143809 | 9/1983 | Japan . |
| 4,917,696 | 4/1990 | De Jonckheere ................... 604/385.2 | | 59-165407 | 11/1984 | Japan ............................. A41B 13/08 |
| 4,936,840 | 6/1990 | Proxmire .............................. 604/385.2 | | 60-9908 | 1/1985 | Japan . |
| 4,938,753 | 7/1990 | Van Gompel et al. .............. 604/385.2 | | 63-131710 | 8/1988 | Japan . |
| 4,938,754 | 7/1990 | Mesek .................................. 604/385.2 | | 63-61402 | 11/1988 | Japan ............................. A41B 13/02 |
| 4,938,757 | 7/1990 | Van Gompel et al. ................. 604/396 | | 55-103208 | 10/1995 | Japan . |
| 4,940,464 | 7/1990 | Van Gompel et al. ................. 604/396 | | 56-70812 | 10/1995 | Japan . |
| 4,963,140 | 10/1990 | Robertson et al. ...................... 604/389 | | 59-88407 | 11/1995 | Japan . |
| 4,973,326 | 11/1990 | Wood et al. ............................ 604/391 | | 493819 | 10/1938 | United Kingdom . |
| 4,978,570 | 12/1990 | Heyn et al. .............................. 428/231 | | 678769 | 9/1952 | United Kingdom . |
| 4,981,480 | 1/1991 | Gaudet et al . ........................... 604/386 | | 918084 | 2/1963 | United Kingdom . |
| 4,988,344 | 1/1991 | Reising et al. ........................... 604/368 | | 1067730 | 5/1967 | United Kingdom . |
| 4,988,346 | 1/1991 | Pfefferkorn ............................. 604/389 | | 1095397 | 12/1967 | United Kingdom . |
| 4,988,560 | 1/1991 | Meyer et al. ............................ 428/297 | | 1299897 | 12/1972 | United Kingdom . |
| 4,994,054 | 2/1991 | Pigneul et al. .......................... 604/391 | | 1318957 | 5/1973 | United Kingdom . |
| 5,019,065 | 5/1991 | Scripps ................................ 604/385.1 | | 1326098 | 8/1973 | United Kingdom . |
| 5,019,072 | 5/1991 | Polski .................................... 604/389 | | 1428572 | 3/1976 | United Kingdom . |
| 5,019,073 | 5/1991 | Roessler et al. ......................... 604/391 | | 1430747 | 4/1976 | United Kingdom . |
| 5,053,028 | 10/1991 | Zoia et al. ............................ 604/385.1 | | 1516287 | 7/1978 | United Kingdom . |
| 5,108,384 | 4/1992 | Goulait ................................... 604/390 | | 1523018 | 8/1978 | United Kingdom . |
| 5,176,671 | 1/1993 | Roessler et al. ......................... 604/386 | | 2035053 | 6/1980 | United Kingdom . |
| 5,242,436 | 9/1993 | Weil et al. ........................... 604/385.2 | | 2074011 | 10/1981 | United Kingdom . |
| 5,279,604 | 1/1994 | Robertson et al. ...................... 604/389 | | 2091986 | 8/1982 | United Kingdom . |
| 5,318,555 | 6/1994 | Siebers et al. ........................... 604/390 | | 2101875 | 1/1983 | United Kingdom . |
| 5,403,302 | 4/1995 | Roessler et al. ......................... 604/391 | | 2 129 689 | 5/1984 | United Kingdom ........... A41B 13/02 |
| B1 3,860,003 | 4/1989 | Buell ................................... 604/385.2 | | 2131346 | 6/1984 | United Kingdom . |
| B1 4,315,508 | 11/1988 | Bolick .................................... 604/392 | | 2135568 | 9/1984 | United Kingdom . |
| | | | | 2142241 | 1/1985 | United Kingdom . |

FOREIGN PATENT DOCUMENTS

| | | |
|---|---|---|
| 0 187 725 B1 | 7/1986 | European Pat. Off. . |
| 0191355A1 | 8/1986 | European Pat. Off. . |
| 0 194 453 A1 | 9/1986 | European Pat. Off. . |
| 0233364A2 | 8/1987 | European Pat. Off. . |
| 0 235 014 B1 | 9/1987 | European Pat. Off. . |
| 0 240 213 A1 | 10/1987 | European Pat. Off. . |
| 0 262 447 A2 | 4/1988 | European Pat. Off. . |
| 0 276 970 A2 | 8/1988 | European Pat. Off. . |
| 0276890A2 | 8/1988 | European Pat. Off. . |
| 0278866A1 | 8/1988 | European Pat. Off. . |
| 0323040 | 5/1989 | European Pat. Off. . |
| 0319249A1 | 6/1989 | European Pat. Off. . |
| 0321232A1 | 6/1989 | European Pat. Off. . |
| 0321234A1 | 6/1989 | European Pat. Off. . |
| 0 324 577 A1 | 7/1989 | European Pat. Off. . |
| 0 324 578 A1 | 7/1989 | European Pat. Off. . |
| 0338680A2 | 10/1989 | European Pat. Off. . |
| 0374730A2 | 6/1990 | European Pat. Off. . |
| 0396050A2 | 11/1990 | European Pat. Off. . |
| 0403832A1 | 12/1990 | European Pat. Off. . |
| 0 476 992 A1 | 3/1992 | European Pat. Off. . |
| 0 529 681 A1 | 3/1993 | European Pat. Off. . |
| 2 105 683 | 4/1972 | France . |
| 2 335 165 | 7/1977 | France . |
| 2 558 691 | 8/1985 | France . |
| 2 564 298 | 11/1985 | France . |
| 2 594 650 | 8/1987 | France . |

| | | |
|---|---|---|
| 2142242 | 1/1985 | United Kingdom . |
| 2142541 | 1/1985 | United Kingdom . |
| 2142542 | 1/1985 | United Kingdom . |
| 2144637 | 3/1985 | United Kingdom . |
| 2148095 | 5/1985 | United Kingdom . |
| 2164542 | 3/1986 | United Kingdom . |
| 2165457 | 4/1986 | United Kingdom . |
| 2185383 | 7/1987 | United Kingdom . |
| 2209672 | 5/1989 | United Kingdom . |
| 2233876 | 1/1991 | United Kingdom . |
| WO 83/03754 | 11/1983 | WIPO . |
| WO84/04242 | 11/1984 | WIPO . |
| WO 86/02263 | 4/1986 | WIPO . |
| WO95/25496 | 9/1995 | WIPO . |

OTHER PUBLICATIONS

"Poly–Lock Fastener Has Industrial Applications," *Industrial Fabrics Products Review,* Nov. 1986, pp. 62, 64.

Instruction panel for PAMPERS® Phases diapers, with Warning, Caution, Disposal information, Packaging Information, and Product Information, 1990.

Communication—European Search Report—EP 91 12 1581.

"Self–Adhering Nylon Tapes" by Maurice Gershman, M.D. *Journal of the American Medical Association,* vol. 168, No. 7, Oct. 18, 1958.

ABSORBENT ARTICLE HAVING AN IMPROVED FASTENING SYSTEM

CROSS-REFERENCE TO RELATED APPLICATIONS

This is a division of application Ser. No. 07/906,016, filed Jun. 26, 1992, now U.S. Pat. No. 5,318,555; which is a continuation-in-part of Ser. No. 07/628,251, filed Dec. 17, 1990, and now abandoned. This is also a continuation-in-part of application Ser. No. 07/954,094, filed Sep. 30, 1992, by Thomas H. Roessler, Bruce M. Siebers, Robert L. Popp and Charles R. Fallen, now U.S. Pat. No. 5,403,302; which is a division of Ser. No. 07/627,874, filed Dec. 13, 1990, by Thomas H. Roessler, Bruce M. Siebers, Robert L. Popp and Charles R. Fallen, now U.S. Pat. No. 5,176,671; which is a continuation of Ser. No. 07/287,746, filed Dec. 20, 1988, and now abandoned.

BACKGROUND OF THE INVENTION

The present invention pertains to diapers, incontinence garments, and the like, and more specifically to a disposable diaper, disposable incontinence garment, and the like in which attachment is accomplished with an improved mechanical fastening system.

Diapers or incontinence garments generally comprise a liquid-impermeable barrier sheet, a liquid-permeable bodyside liner, and an absorbent medium therebetween. They may generally include some type of attaching system for fitting the diaper or garment to the wearer. The present invention is intended for use with these types of articles, and also with other types of articles that require some type of attaching feature, such articles being surgical gowns, and other personal care or health care garments.

Mechanical attachments, such as hook-and-loop systems, have been used on garments in the past. However, various limitations have prevented the widespread commercialization of these systems on disposable garments or other disposable articles. The most apparent limitations to the commercialization include the cost of the system and the functionality of that system. Typically, the cost and functionality of the system is a tradeoff. In other words, greater functionality and performance can be achieved by using more expensive materials.

Generally, hook-and-loop systems fail in the "peel" mode. For example, a peel mode exists when one component is held stationary, while the second component is pulled off the first component sequentially. When two attaching components, such as a plurality of hooks and a plurality of loops, are disengaged in the peel mode, the hooks and loops are progressively separated. That is, each row or line of hooks is disengaged a little at a time until all of the hooks are disengaged from their respective loops. The peel performance of hook-and-loop systems is very sensitive to the cost/performance ratio. Generally, to obtain higher peel, a higher basis weight loop must be used which ultimately translates to more loops, thicker fabric, and greater overall cost.

A "shear" mode failure, in comparison, exists when the two components are being pulled apart by oppositely directed forces lying in the same plane. The shear mode action is a sliding, linear action, in contrast to the peel mode which is a curvilinear type of motion or action.

A "latching" mode failure exists when the two components are being pulled apart by oppositely directed forces acting generally perpendicular to the plane of the components.

SUMMARY OF THE INVENTION

The present invention provides various features and techniques to improve the performance of hook-and-loop systems.

In one embodiment of the present invention there is provided an absorbent article comprising a composite including a substrate, an absorbent, and front and back end portions. A first releasably engageable member is on the back end portion, and a second releasably engageable member is with the front end portion. A buckling mechanism joins the second releasably engageable member to the front end portion.

In another embodiment of the present invention the back end portion has an attaching member, and a foldable trapping panel is on the front end portion. The trapping panel comprises a base panel and a flap panel, and the attaching member is releasably engageable between them.

In yet another embodiment of the present invention a tensioning mechanism applies tension to the first and second releasably engageable members.

BRIEF DESCRIPTION OF THE DRAWINGS

The above-mentioned and other features and objects of this invention, and the manner of attaining them, will become more apparent and the invention itself will be better understood by reference to the following description of the embodiments of the invention taken in conjunction with the accompanying drawings, wherein.

DETAILED DESCRIPTION

Although it is contemplated that the present invention is operable in a baby diaper, child's training pant, adult incontinence products, and other personal or health care products, the present description will be made in terms of a baby diaper for ease of explanation and illustration.

Figure 1:
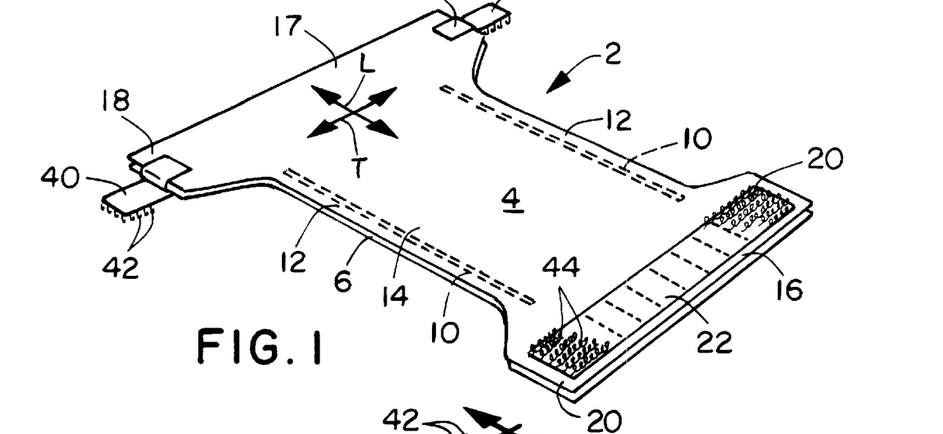
FIG. 1 is a perspective view of the back of a diaper incorporating some principles of the present invention.
Figure 2:
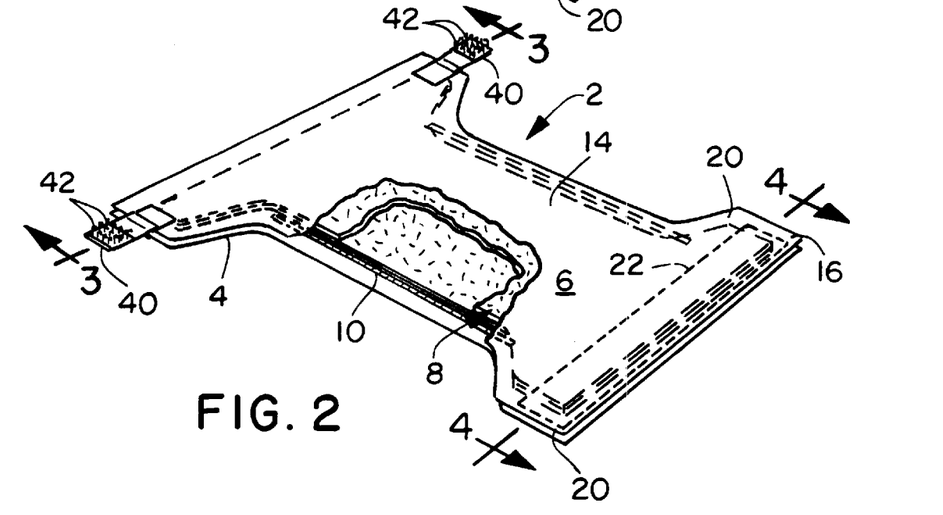
FIG. 2 is a perspective front view of the diaper in FIG. 1 partially broken away.

Referring to FIGS. 1–4, diaper 2 generally comprises backsheet 4, topsheet 6, and absorbent medium 8 therebetween. Leg elastics 10 are joined to side margins 12 of diaper 2 in order to gather or shirr at least intermediate portion 14 of diaper 2. Diaper 2 further comprises a front waist portion 16, rear waist portion 17, and ear portions 18 that are generally integral with rear waist portion 17. As can be seen in FIGS. 1 and 2, intermediate portion 14 has a more narrow width that front and rear waist portions 16, 17, thereby giving diaper 2 a generally hour-glass shape. In FIG. 1, the arrow designated L represents the length dimension of diaper 2 and the machine direction in the manufacture of diaper 2, and the arrow perpendicular thereto designated as T indicates the width of diaper 2, as well the cross direction of the diaper during the manufacturing process.

Front waist portion 16 includes ear sections 20 which have disposed therebetween loop panel 22, which comprises the loop component of the hook-and-loop system. Loop panel 22 can be a fabric material manufactured to have a raised loop construction in which the fabric is stabilized, i.e., the individual loops are erect from the fabric's base, through a napping treatment. Panel 22 can also be any suitable material having non-woven loops thereon. Loop panel 22 is attached to front waist portion 16 of backsheet 4 such that the loops extend outwardly therefrom. The geometric shape of loop panel 22 can be any desired shape, such as rectangular, irregular, diamond, triangular, circular, oval, chevron, or the like. As illustrated, loop panel 22 is generally rectangular in shape.

Referring to FIGS. 1–6, loop panel 22 is bonded or attached to backsheet 4 in a manner that is unique and results in enhanced mechanical attaching, specifically increasing the peel, shear, and latching strengths of the attaching system. Rather than bonding the entire undersurface of loop panel 22 to the surface of backsheet 4, only discrete or predetermined sections of panel 22 are attached or bonded to backsheet 4, thereby leaving portions of loop panel 22 unattached and free to move relative to backsheet 4. By thus controlling the bonding or attaching pattern of loop panel 22, the peel, shear, and latching properties of the hook-and-loop system are significantly enhanced, as graphically illustrated in FIG. 7.

Figure 5:
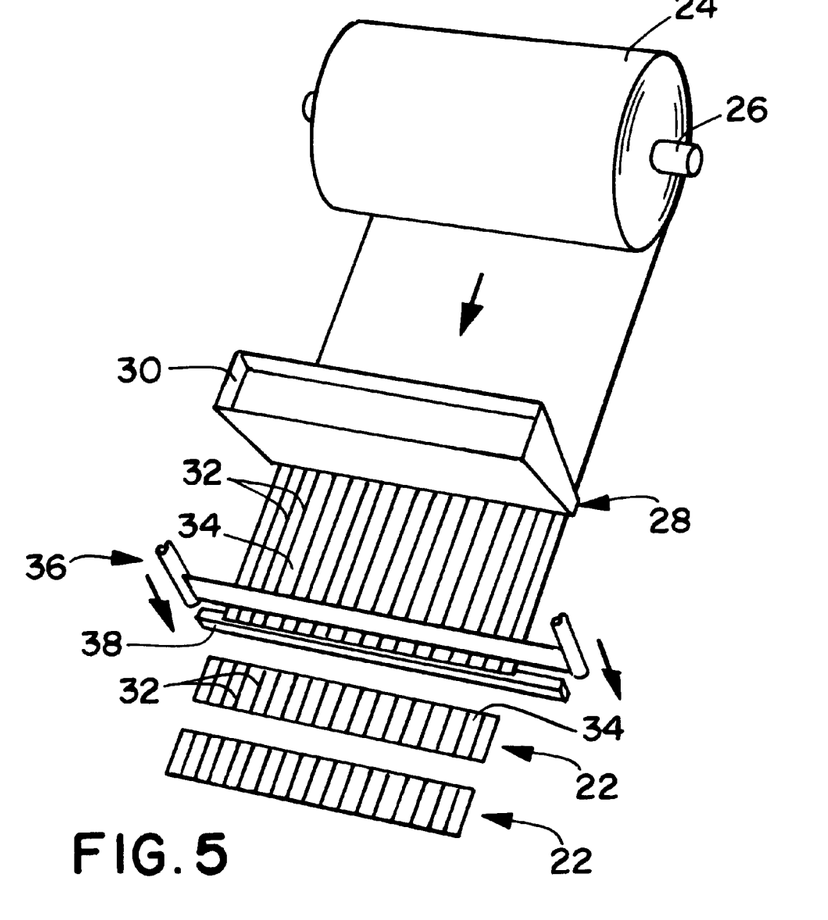
FIG. 5 is a schematic of an apparatus for applying adhesive beads in a spaced-apart fashion upon a material sheet.
Figure 6:
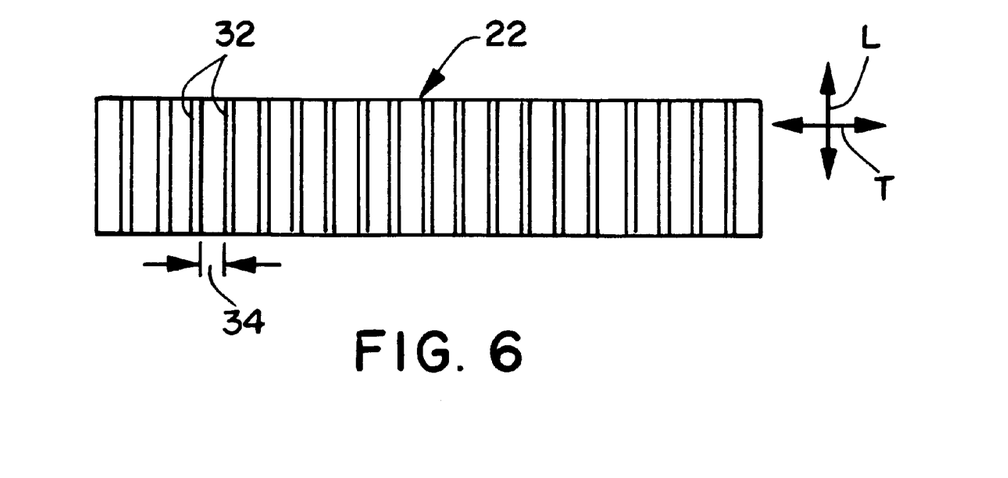
FIG. 6 is a plan view of the applied adhesive beads on the material sheet.
Figure 7:
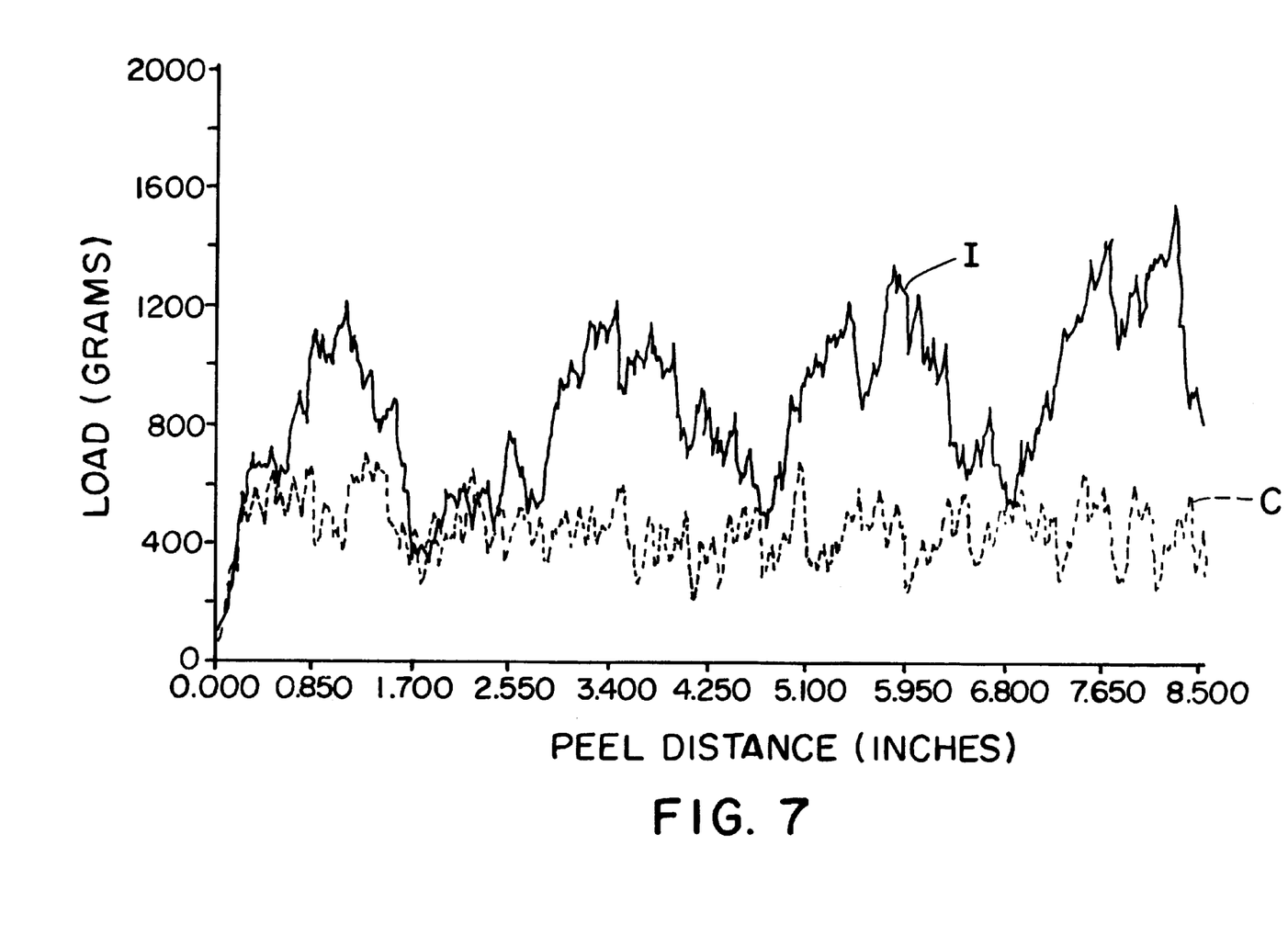
FIG. 7 is a graph comparing the closure force of a conventional hook-and-loop system and a hook-and-loop system of the present invention.

Referring specifically to FIGS. 5 and 6, a roll of loop material 24 is unwound from reel 26 and passed below hot melt die 28 that is in fluid communication with hopper 30, which contains a hot melt adhesive. The hot melt adhesive is applied by running loop material 24 under die 28 which applies spaced-apart beads 32 of adhesive onto loop material 24 in the machine direction, as illustrated by the arrow in FIG. 5. Since beads 32 are spaced apart, they naturally form spaces 34 therebetween.

The apparatus in FIG. 5 further includes a cutting device 36 including blade 38, which is reciprocated downwardly to cut a plurality of loop panels 22 from loop material 24.

The adhesive beads 32 range in their width from about 1 millimeter to about 15 millimeters, and the width of each space 34 is generally in the range from about 1 millimeter to about 30 millimeters. In one preferred embodiment, beads 32 are 3 millimeters in width, and are spaced about 3 millimeters apart, i.e., spaces 34 have a width of about 3 millimeters. Loop panel 22 is then attached to backsheet 4 between ear sections 20, as illustrated in FIG. 1.

As illustrated in FIGS. 5 and 6, adhesive beads 32 are applied in a parallel, linear fashion, but the present invention contemplates application of adhesive beads 32 in any desired pattern as long as the resulting application produces spaced-apart areas of adhesive, such as beads 32.

Figure 3:
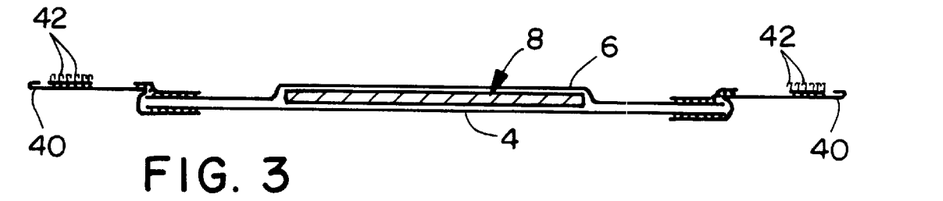
FIG. 3 is a cross-sectional view of FIG. 2 taken along line 3—3 and viewed in the direction of the arrows.
Figure 4:
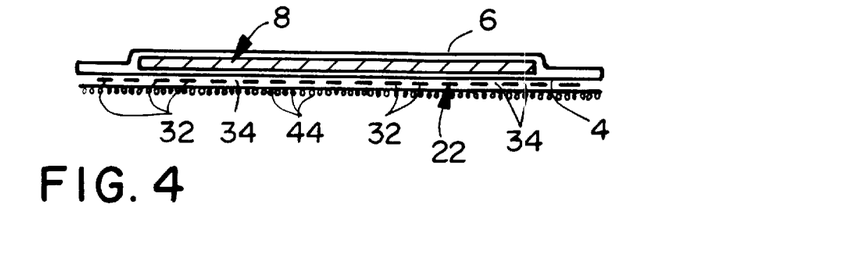
FIG. 4 is a cross-sectional view of FIG. 2 taken along line 4—4 and viewed in the direction of the arrows.
Figure 8:
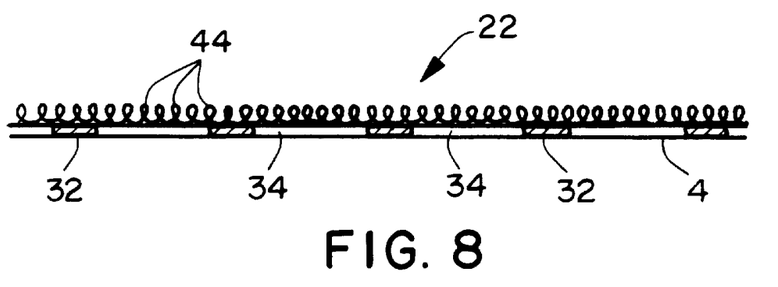
FIG. 8 is an enlarged side elevational view illustrating the attachment of a loop material on a substrate in accordance with the present invention.
Figure 9:
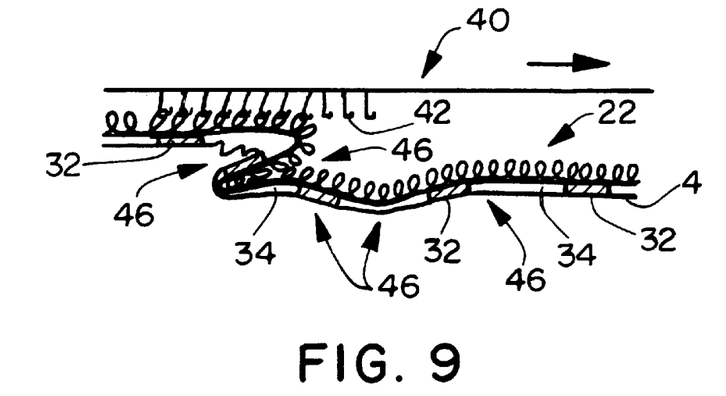
FIG. 9 is an enlarged side elevational view of the loop material in FIG. 8 in a buckled, tensioned state.

Referring to FIGS. 1–4, 8, 9, each ear portion 18 includes a hook tab 40 extending outwardly thereon and including a plurality of hook members 42 for engaging a plurality of loop members 44. As illustrated in FIG. 3 and FIG. 9, each individual hook member 42 can face a single direction. However, the present invention contemplates that the hook members 22 can be oriented in two or more directions. For example, a first predetermined set of rows of hook members 42 could face inwardly, as illustrated in FIG. 3, while other predetermined remaining rows can have their hook members 42 facing in an opposite direction. Alternatively, individual ones of hook members 42 can be oriented in any different number of directions as required.

Hook members 42 can have any desired geometry or shape, and can be made of any suitable material. Hook members 42 can be made of a nylon material, or of materials represented in FIG. 15 as unidirectional HTH 706, HTH 707, or HTH 708 that can be purchased from Velcro Industries B.V., Amsterdam, Netherlands or affiliates thereof. Shapes of members 42 can be hook-, mushroom-shaped, or any other desired shape. Hook member density on a respective hook tab 40 is generally within the range of about 30 to about 160 hooks per square centimeter, and preferably about 115 hooks per square centimeter. Each hook tab 40 also may have a row density within the range of about 3 to about 30 rows per lineal centimeter of width, and preferably a row density of about 15 rows per lineal centimeter. Naturally, these ranges of hook density and row density can vary and be dependent upon the peel and shear characteristics of the type and geometry of material used.

The present invention contemplates interchanging the position or placement of the hook members and loop members on their particular garment or article.

Referring now to FIG. 8, there is illustrated an enlarged side elevational view of backsheet 4 having attached thereto loop panel 22 and its loop members 44 by the spaced-apart adhesive beads 32. Between beads 32 are spaces 34 in which loop panel 22 is unattached to backsheet 4. Upon engaging a respective hook tab 40 to loop panel 22 such that hook members 42 engage loop members 44, and upon application of a tension as illustrated by the arrow in FIG. 9, loop panel 22 will distort or flex with a plurality of buckles 46. This generally results in an increase in the peel, shear, and/or latching strengths between hook tabs 40 and loop panel 22. As graphically illustrated in FIG. 7, graph line C illustrates the closure force of a conventional hook-and-loop system in which the loop panel is totally adhered to its substrate. In contrast, graph line I illustrates the increase in closure force provided by the present invention in which loop panel 22 is intermittently or discretely attached to its backsheet 4. Without being bound to any specific theory or mechanism, it has been found that the increase in peel, shear, and latching strengths results from intermittent attachment of loop panel 22 to backsheet 4, thereby forming a plurality of buckles 46 when hook tabs 40 are engaged under tension to loop panel 22. A preferred tension range is between about 50 grams per inch and about 500 grams per inch.

Figure 10:
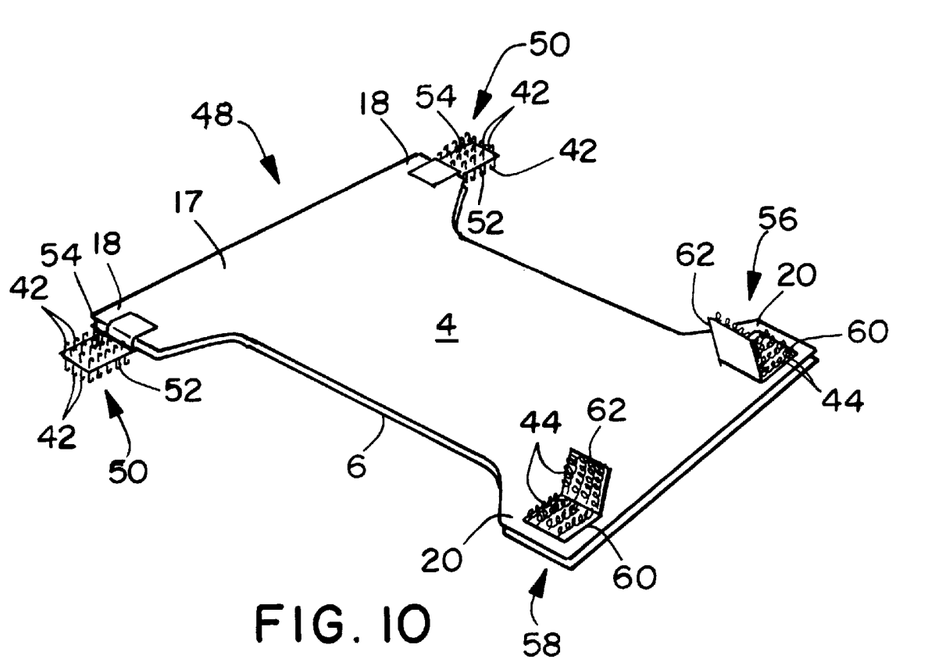
FIG. 10 is a perspective view of the back of a diaper incorporating other principles of the present invention.

Referring now to FIG. 10, diaper 48 illustrates another embodiment of the present invention. Diaper 48 is identical to diaper 2 except in the following description. Each ear portion 18 has joined thereto hook tab 50 having a plurality of hook members 42 disposed on both inner surface 52 and outer surface 54 of a respective hook tab 50. Generally, hook tab 50 can be made of a stretchable or elastomeric material, or hook tab 50 can be joined to a respective ear portion 18 by an intermediate strip of stretchable or elastic material that joins hook tab 50 to ear portion 18.

Front waist portion 16 of backsheet 4 has disposed thereon two separate loop panels 56, 58. Since loop panels 56, 58 are identical, a description of only loop panel 56 will be made. Loop panel 56 includes loop panel base 60 joined to backsheet 4 and loop panel flap 62 which is hingedly connected to loop panel base 60, as illustrated in FIG. 10. This permits loop panel flap 62 to be folded back and forth between a generally unfolded position, in which it is substantially coplanar with loop panel base 60, and a folded position, in which it is folded over and on top of loop panel base 60 such that their respective loop members 44 are in mutually facing relationship.

Figure 11:
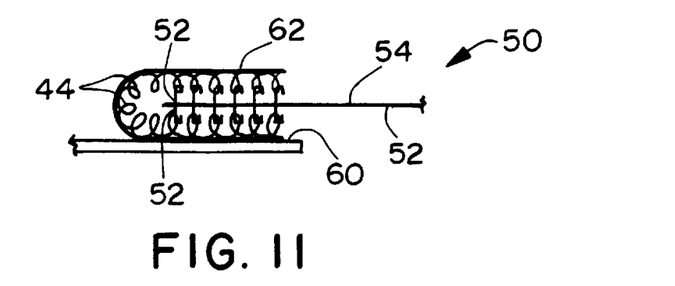
FIG. 11 is an enlarged side elevational view illustrating the closed position of the attaching system illustrated in FIG. 10.

Referring to FIGS. 10 and 11, upon placing diaper 48 about the wearer, each ear portion 18 is drawn around the waist section of the wearer and a respective hook tab 50 is stretched, i.e., placed under tension, as necessary for a proper fit, and placed against loop panel base 60 to engage hook members 42 on inner surface 52 with loop members 44 of loop panel base 60. Loop panel flap 62 is then folded over and engaged with hook tab 50 such that loop members 44 of loop panel flaps 62 engage hook members 52 on outer surface 54 of hook tab 40. Although FIG. 11 illustrates hook members 52 as having their open or mouth ends oriented in the same direction, hook members 52 may be multiply directed as required to provide the desired attachment.

Figure 12:
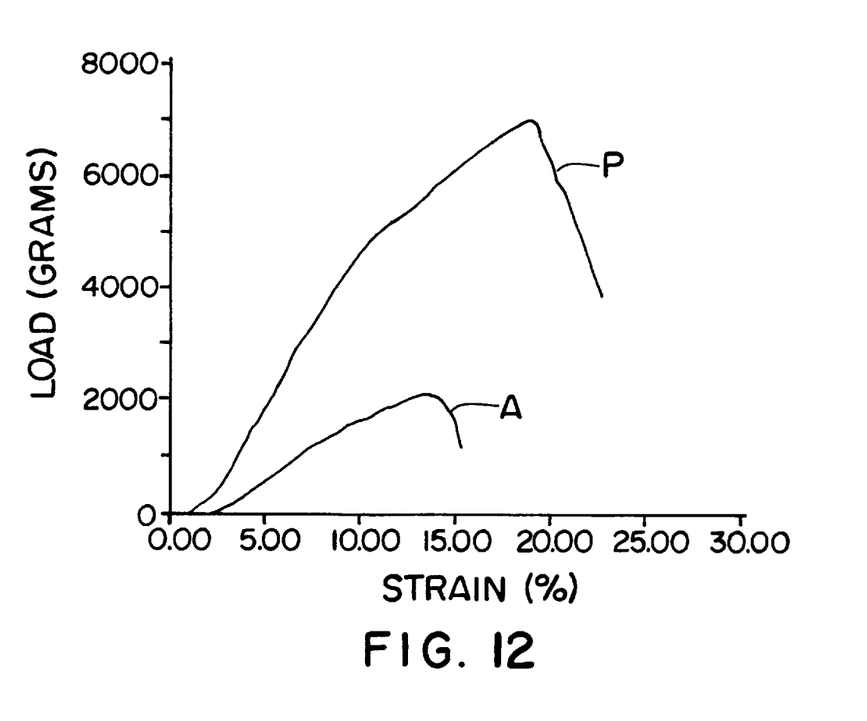
FIG. 12 is a graph comparing the closure force of a hook-and-loop system without a trap feature and a hook-and-loop system incorporating a trap feature of the present invention.

Referring to FIG. 12, graph line A represents the closure force of a conventional hook-and-loop system without a loop panel flap, and graph line P illustrates the present invention in which loop panel flap 62 and loop panel base 60 trap hook members 52 of hook tab 50.

Figure 13A:
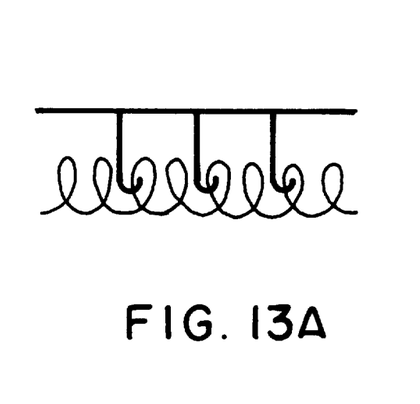
FIG. 13A is an enlarged side elevational view illustrating a hook-and-loop system in a conventional unpensioned state.
Figure 13B:
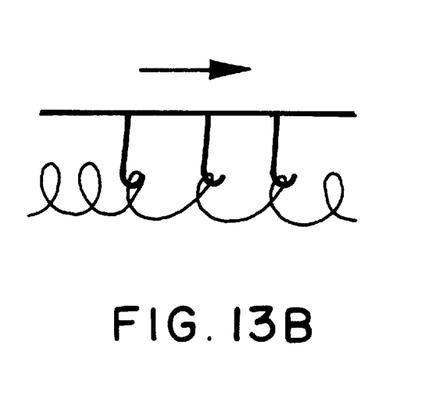
FIG. 13B is an enlarged side elevational view illustrating a hook-and-loop system of the present invention in a tensioned state.

Referring to FIG. 13A, a conventional hook-and-loop system in an unpensioned state is illustrated. Because of the unpensioned state, there is a certain amount of looseness or play between individual hooks and loops that can result in a less than desirable fastening system. In contrast, FIG. 13B illustrates the hook-and-loop system of the present invention in a tensioned state that causes the hooks to be engaged firmly without play with their respective loops. This increases the stability and performance of the fastening system.

Figure 14:
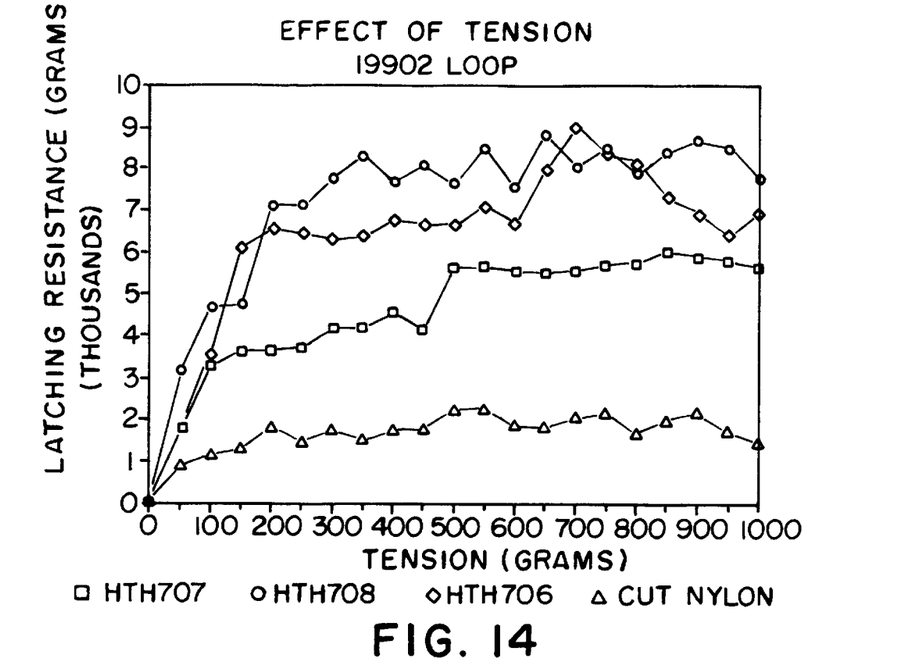
FIG. 14 is a graph illustrating increases in latching forces as tension is increased on the system.
Figure 15:
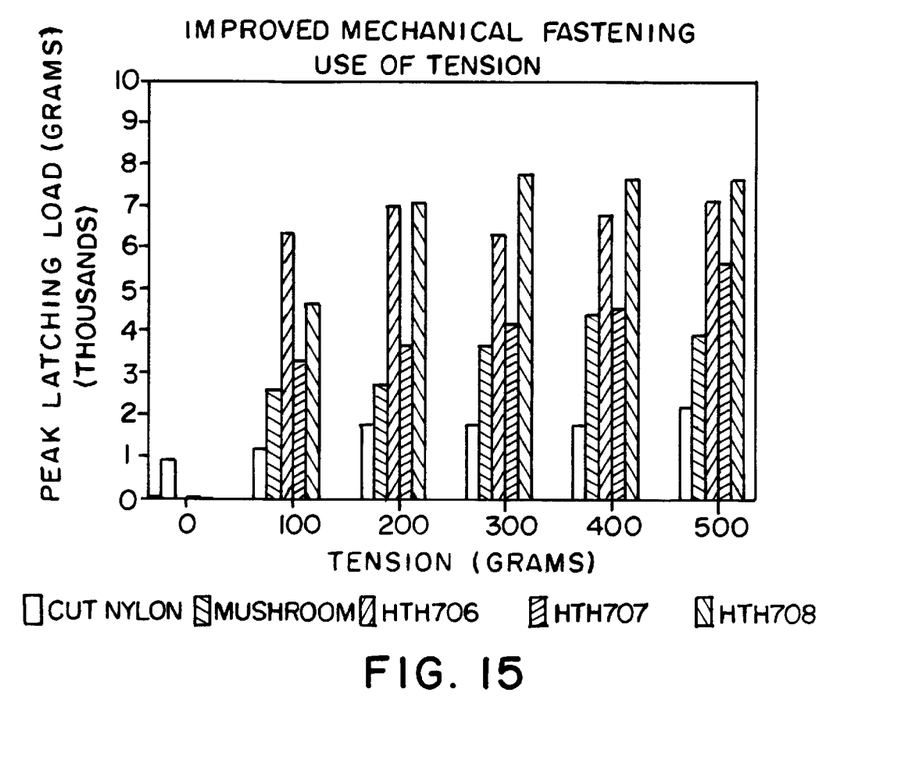
FIG. 15 is a graph comparing improved mechanical fastening for different hook types under varying tensions.

For example, FIGS. 14 and 15 illustrate the increase in latching forces for hooks made of different materials as tension is increased. As shown in FIG. 14, the hook members may exhibit a latching resistance, when engaged with a 19902 loop under 200 grams tension, of at least 3000 grams, or even of at least 5000 grams. Thus, regardless of the hook material or article with which the fastening system of the present invention may be used, tension enhances the performance of all systems to some degree.

TEST PROCEDURES

Peel Test Procedure

Peel is determined according to ASTM Designation D1876-72, "Standard Test Methods for Peel Resistance of Adhesives (T-Peel Test)", subject to the following modification: No test panels are used; hook-and-loop materials are directly engaged and are not mounted on any other substrate unless specified. Test direction of the materials should be noted. No panels are used. The engaged test materials are rolled five cycles; where one cycle equals once in each direction. The hook material is clamped into the upper jaw and the loop material is clamped into the lower jaw.

Shear Test Procedure

Shear is determined according to ASTM Designation D3654-82, "Standard Test Method for Holding Power of Pressure-Sensitive Tapes", and which is subject to the following modification: In relation to the test, the closure is placed under an increasing load. The system being tested is a hook-and-loop closure system. The apparatus should include an "INSTRON" or equivalent tensile tester. In carrying out the procedure, test direction of the materials should be noted. The test materials are rolled five cycles (one square inch), where one cycle equals once in each direction. The hook material is clamped into the lower jaw of the INSTRON tensile tester. The engaged system (hook-and-loop) is pulled until failure. In doing calculations, the peak load is determined and recorded in grams.

Latching Test Procedure

Latching force is measured by applying a hook material to a loop material, applying a lateral force to the interface between the hook and loop materials, and then separating the hook and loop materials with a vertical force. The amount of vertical force necessary to separate the two materials is the peak force, or load in grams, and determines the latching force. This test method measures the effect of tension, such as that applied by an elastic member, on a hook-and-loop closure system. In this test, the phrase "latching force" means the force required to disengage a hook material from a loop material resulting from a pull perpendicular to the plane of attachment of the materials to which a fixed lateral force is applied. The phrase "lateral force" means a force applied in parallel to the interface of the hook and loop materials, and the phrase "vertical force" means a force applied perpendicular to the interface of the hook and loop materials.

Figure 16:
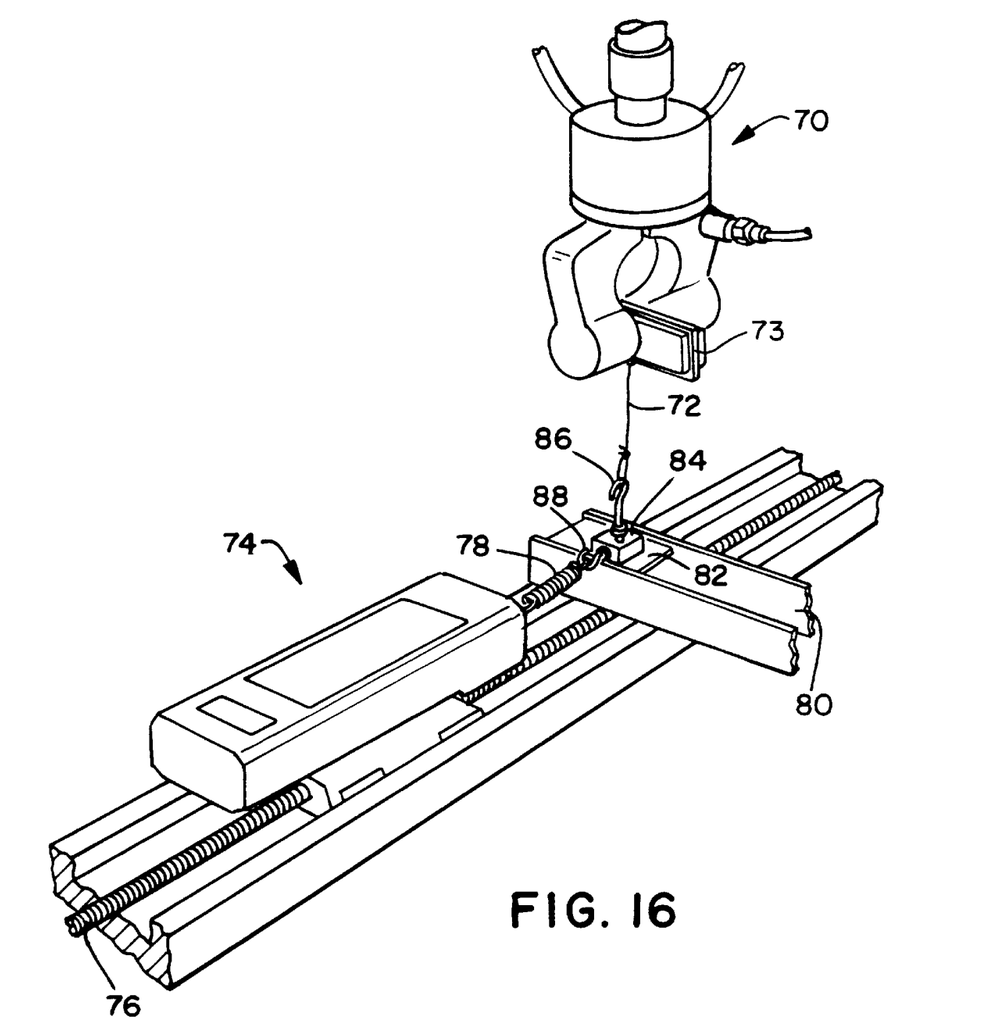
FIG. 16 is an illustration of equipment used with the described latching test procedure.

Referring to FIG. 16, there is illustrated the upper grips 70 of a suitable tensile testing machine, such as an Instron tensile tester commercially available from Instron Corporation, Canton, Mass. A suspension line 72 is connected to a plate 73 held by the upper grips 70 of the tensile testing machine and hangs downwardly therefrom. Force gauge 74 is horizontally mounted and is selectively moveable in the horizontal by means of threaded rod 76. Force gauge 74 includes a spring 78. Latching force test fixture 80 is used to fix a stainless steel test panel 82 in a stationary position. Hook material mounting block 84 includes a vertically oriented eye screw 86 connected to suspension line 72 and a horizontally disposed eye screw 88 connected to spring 78.

A hook-and-loop closure system is tested by mounting the hook material on the undersurface of hook material mounting block 84 and mounting a loop material on the top surface of test panel 82, and then utilizing a lateral force applied by threaded rod 76 and force gauge 74 and a vertical force applied by upper grips 70 of the tensile testing machine. This test method is used to analyze the effect of tension on a hook-and-loop closure system particularly when the hooks are oriented in the direction of the applied tension force.

The tensile testing machine used can be any suitable machine that can supply a constant rate of extension having a rate of traverse of about 305 millimeters per minute. Test panel 82 preferably has the dimensions of 51 millimeters× 152 millimeters. Hook material mounting block 84 should be made of aluminum having a mounting surface with a dimension of about 25 millimeters×25 millimeters.

The test procedure occurs in generally two stages, one being the preparation of the test specimens and the other being the determination of the latching force. The preparation of test specimens includes cutting a 25 millimeter square specimen of the hook material and attaching it to the hook material mounting block 84 with a two-sided adhesive tape that has an adhesive strength greater than the hook-and-loop closure system being tested. The hook material should be mounted in a manner that will enable any directionality of the hooks to be utilized in the most efficient manner with regard to the tensioning force. The loop material is cut to have the dimensions of about 37.5 millimeters× 152 millimeters and then attached to the stainless steel test panel 82 so that there is approximately 6 millimeters distance between the edge of the loop specimen and the edge of the test panel 82. Again, a two-sided adhesive tape is used to attach the loop material with the tape having a greater adhesive strength than the hook-and-loop closure system.

The determination of the latching force is accomplished by first inserting an empty test panel 82 in latching force test fixture 80. An empty hook material mounting block 84 is centered in the upper grips 70 by means of suspension line 72 and plate 73. Hook material mounting block 84 is then positioned to slightly rest on test panel 82 with minimal slack in suspension line 72. The empty test panel is then replaced with a test panel 82 having the loop material attached thereto. Hook material mounting block 84, which has the material attached to its undersurface, is then placed on top of the loop material without applying any pressure. A lateral force (for example, about 500 grams) is then selectively applied by means of force gauge 74 and threaded rod 76. Thereafter, the tensile testing machine is activated to apply a vertical force until the hook and loop materials are separated. The applied vertical force, at which the hook and loop materials separate, is the latching force for the applied lateral force. The peak load is reported as latching force (sometimes referred to as "latching resistance" or "peak latching load").

While this invention has been described as having preferred embodiments, it will be understood that it is capable of further modifications. This application is therefore intended to cover any equivalents, variations, uses, or adaptations of the invention following the general principles thereof, and including such departures from the present disclosure as come within known or customary practice in the art to which this invention pertains and fall within the limits of the appended claims.

What is claimed is:

1. An absorbent article, comprising:
    a composite comprising a substrate and an absorbent on said substrate,
    said composite further comprising oppositely disposed front and back end portions,
    an attaching member on said back end portion of said composite, said attaching member comprising a plurality of hook members, and
    a foldable trapping panel on said front end portion of said composite, and comprising a base panel stationary on said front end portion and comprising a plurality of loop members and a flap panel freely foldable relative to said base panel and comprising a plurality of loop members,
    said attaching member being releasably engageable between said base panel and said flap panel.

2. An absorbent article, comprising:
    a composite comprising a substrate and an absorbent on said substrate, said composite further comprising oppositely disposed front and back end portions,
    an attaching member on said back end portion of said composite said attaching member comprising a plurality of loop members, and
    a foldable trapping panel on said front end portion of said composite, and comprising a base panel stationary on said front end portion and comprising a plurality of hook members and a flap panel freely foldable relative to said base panel and comprising a plurality of hook members,
    said attaching member being releasably engageable between said base panel and said flap panel.

3. The article of claim 1 or 2 wherein said hook members are oriented in one direction.

4. The article of claim 1 or 2 wherein said hook members are oriented in multiple directions.

5. The article of claim 1 or 2 wherein said attaching member is stretchable.

6. The article of claim 1 or 2 further comprising a buckling means joining said base panel to said front end portion, said buckling means comprising a plurality of spaced-apart coupling means for intermittently coupling said base panel to said front end portion.

7. An absorbent article, comprising:
    a composite comprising a substrate and an absorbent on said substrate,
    said composite further comprising oppositely disposed front and back end portions,
    a first releasably engageable member on said back end portion of said composite, said first releasably engageable member comprising a hook tab comprising a plurality of hook members,
    a second releasably engageable member on said front end portion of said composite, said second releasably engageable member comprising a plurality of loop members, said second releasably engageable member being distortable,
    said first and second releasably engageable members being releasably engageable together,
    an elastic material for applying a tension to said first and second releasably engageable members when said hook members and said loop members are enlarged whereby said second releasably engageable member is distorted, and
    wherein said hook members exhibit a latching resistance, when engaged with a 19902 loop under 200 grams tension, of at least 3,000 grams.

8. An absorbent article, comprising:
    a composite comprising a substrate and an absorbent on said substrate,
    said composite further comprising oppositely disposed front and back end portions,
    a first releasably engageable member on said back end portion of said composite, said first releasably engageable member comprising a hook tab comprising a plurality of hook members,
    a second releasably engageable member on said front end portion of said composite, said second releasably engageable member comprising a plurality of loop members, said second releasably engageable member being distortable, said first and second releasably engageable members being releasably engageable together, an elastic material for applying a tension to said first and second releasably engageable members when said hook members and said loop members are engaged whereby said second releasably engageable member is distorted, and wherein said hook members exhibit a latching resistance, when engaged with a 19902 loop under 200 grams tension, of at least 5,000 grams.

9. A diaper, said diaper defining a front waist portion, a rear waist portion and an intermediate portion between said front waist portion and said rear waist portion, said diaper comprising:

a back sheet;

a top sheet;

an absorbent medium therebetween;

a distortable loop panel comprising a plurality of loop members disposed on said front waist portion;

two hook tabs, comprising a plurality of hook members for engaging said loop members, each hook tab extending outwardly from said rear waist portion, said hook members being hook- or mushroom-shaped;

a tensioning mechanism for engaging said hook tabs to said loop panel under tension whereby said loop panel is distorted; and wherein said hook members exhibit a latching resistance, when engaged with a 19902 loop under 200 grams tension, of at least 3,000 grams.

10. A diaper, said diaper defining a front waist portion, a rear waist portion and an intermediate portion between said front waist portion and said rear waist portion, said diaper comprising:

a back sheet;

a top sheet;

an absorbent medium therebetween;

a distortable loop panel comprising a plurality of loop members disposed on said front waist portion;

two hook tabs, comprising a plurality of hook members for engaging said loop members, each hook tab extending outwardly from said rear waist portion, said hook members being hook- or mushroom-shaped;

a tensioning mechanism for engaging said hook tabs to said loop panel under tension whereby said loop panel is distorted; and wherein said hook members exhibit a latching resistance, when engaged with a 19902 loop under 200 grams tension, of at least 5,000 grams.

11. An absorbent article, comprising:

a composite comprising a substrate, an absorbent, and front and back end portions;

a first releasably engageable member on said back end portion of said composite, said first releasably engageable member comprising a hook tab comprising a plurality of hook members, said hook tab exhibiting a latching resistance, when engaged with a 19902 loop under 200 grams tension, of at least 3,000 grams, a second releasably engageable member on said front end portion of said composite, said second releasably engageable member comprising a plurality of loop members and said first and second releasably engageable members being releasably engageable together; and an elastic material for applying a tension to said first and second releasably engageable members when said hook members and said loop members are engaged.

12. The article of claim 11 wherein said second releasably engageable member is intermittently attached to said front edge portion of said composite.

13. The article of claim 11 wherein said hook members are engaged under tension to said loop members by said elastic material.

14. The article of claim 11 wherein said hook members are oriented in the direction of the width of the article.

15. The article of claim 11 wherein a tension between about 50 grams per inch and about 500 grams per inch can be applied to said first and second releasably engageable members when said hook members and said loop members are engaged.

16. The article of claim 11 wherein said hook members are hook or mushroom-shaped.

17. The article of claim 16 wherein said hook member density on said hook tab is from about 30 to about 160 hooks per square centimeter.

18. The article of claim 17 wherein said hook member density on said hook tab is about 115 hooks per square centimeter.

19. The article of claim 17 wherein said hook tab has a row density of from about 3 to about 30 rows per lineal centimeter of width.

* * * * *

UNITED STATES PATENT AND TRADEMARK OFFICE
CERTIFICATE OF CORRECTION

PATENT NO. : 5,984,911
DATED : November 16, 1999
INVENTOR(S) : Bruce Michael Siebers, Gary Lee Travis and Thomas Walter Odorzynski It is certified that error appears in the above-identified patent and that said Letters Patent is hereby corrected as shown below:

Column 8,
Line 49, delete "enlarged" and substitute -- engaged --.

Signed and Sealed this

Eleventh Day of February, 2003

JAMES E. ROGAN
*Director of the United States Patent and Trademark Office*